(12) United States Patent
Gil

(10) Patent No.: US 8,109,634 B2
(45) Date of Patent: Feb. 7, 2012

(54) SNAPSHOT SPECTRAL IMAGING OF THE EYE

(76) Inventor: Tamir Gil, Kibbutz Givat Haim Meuchad (IL)

( * ) Notice: Subject to any disclaimer, the term of this patent is extended or adjusted under 35 U.S.C. 154(b) by 117 days.

(21) Appl. No.: 12/398,255

(22) Filed: Mar. 5, 2009

(65) Prior Publication Data

US 2009/0225277 A1 Sep. 10, 2009

Related U.S. Application Data

(60) Provisional application No. 61/064,420, filed on Mar. 5, 2008.

(51) Int. Cl.
*A61B 3/14* (2006.01)
*A61B 3/10* (2006.01)
*A61B 3/00* (2006.01)

(52) U.S. Cl. ............... 351/206; 351/221; 351/246

(58) Field of Classification Search .......... 351/200–246
See application file for complete search history.

(56) References Cited

U.S. PATENT DOCUMENTS

| | | | |
|---|---|---|---|
| 5,539,517 A * | 7/1996 | Cabib et al. | 356/456 |
| 6,088,099 A * | 7/2000 | Cabib et al. | 356/456 |
| 6,276,798 B1 * | 8/2001 | Gil et al. | 351/206 |
| 6,419,361 B2 * | 7/2002 | Cabib et al. | 351/221 |
| 6,456,787 B1 | 9/2002 | Matsumoto et al. | |
| 2001/0033364 A1 * | 10/2001 | Cabib et al. | 351/221 |
| 2002/0001080 A1 | 1/2002 | Miller et al. | |
| 2002/0052551 A1 | 5/2002 | Sinclair et al. | |
| 2003/0007124 A1 | 1/2003 | Levine | |
| 2006/0020184 A1 * | 1/2006 | Woods et al. | 600/319 |
| 2006/0066738 A1 | 3/2006 | Hershey et al. | |
| 2006/0268231 A1 | 11/2006 | Gil et al. | |
| 2007/0002276 A1 | 1/2007 | Hirohara et al. | |
| 2007/0129709 A1 | 6/2007 | Andersen et al. | |
| 2008/0007691 A1 | 1/2008 | Mihashi et al. | |
| 2008/0007692 A1 | 1/2008 | Mihashi et al. | |

FOREIGN PATENT DOCUMENTS

WO 2008/074019 A2 6/2008

OTHER PUBLICATIONS

Hickam et al.; "A Study of Retinal Venous Blood Oxygen Saturation in Human Subjects by Photographic Means"; Circulation, Journal of the American Heart Association; 1963; pp. 375-385; vol. 27, February.

Pittman et al.; "A New Method for the Measurement of Percent Oxyhemoglobin"; Journal of Applied Physiology; Feb. 1975; pp. 315-320; vol. 38; No. 2.

(Continued)

*Primary Examiner* — Mohammed Hasan
(74) *Attorney, Agent, or Firm* — The Webb Law Firm

(57) ABSTRACT

Obtaining spectral images of an eye includes taking an optical system that images eye tissue onto a digital sensor array and optically fitting a multi-spectral filter array and the digital sensor array, wherein the multi-spectral filter array is disposed between the digital sensor array and an optics portion of the optical system. The resulting system facilitates acquisition of a snap-shot image of the eye tissue with the digital sensor array. The snap shot images support estimation of blood oxygen saturation in a retinal tissue. The resulting system can be based on a non-mydriatic fundus camera designed to obtain the retinal images without administration of pupil dilation drops.

21 Claims, 6 Drawing Sheets

OTHER PUBLICATIONS

Van Assendelft; "Spectrophotometry of Haemoglobin Derivatives"; Royal Vangorcum, Ltd., Assen, The Netherlands, Springfield, Il.; 1970; pp. 41-46, February.

Van Norrin et al.: "Spectral Reflectance of the Human Eye"; Vision Res.; 1986; pp. 313-320; vol. 26; No. 2, March.

Delori; "Noninvasive Technique for Oximetry of Blood in Retinal Vessels"; Applied Optics; Mar. 15, 1988; pp. 1113-1125; vol. 27; No. 6.

Delori; "Reflectometry Measurements of Optic Disc Blood Volume"; Ocular Blood Flow in Glaucoma; 1989; pp. 155-163; Kugler & Ghedini Publications; Amsterdam; Berkeley, Milano, March.

Delori et al.; "Spectral Reflectance of the Human Ocular Fundus"; Applied Optics; Mar. 15, 1989; pp. 1061-1077; vol. 28; No. 6.

Schweitzer et al.: "Calibration-Free Measurement of the Oxygen Saturation in Retinal Vessels of Men"; Proc. SPIE; 1995; pp. 210-218; vol. 2393, March.

Yoneya et al.; "Retinal Oxygen Saturation Levels in Patients with Central Retinal Vein Occlusion"; Ophthalmology; Aug. 2002; pp. 1521-1526; vol. 109; No. 8.

Alabboud et al.; "New Spectral Imaging Techniques for Blood Oximetry in the Retina"; Proceedings of SPIE; Jun. 7, 2007; 10 pages; vol. 6631.

Kagemann et al.; "Spectral Oximetry Assessed with High-Speed Ultra-High-Resolution Optical Coherence Tomography"; Journal of Biomedical Optics; Jul./Aug. 2007; pp. 041212-1-41212-8; vol. 12; No. 4.

Hardarson et al.; "Automatic Retinal Oximetry"; Investigative Ophthalmology & Visual Science; Nov. 2006; pp. 5011-5016; vol. 47; No. 11.

Ramella-Roman et al.; "Measurement of Oxygen Saturation in the Retina with a Spectroscopic Sensitive Multi Aperture Camera"; Optics Express; Apr. 28, 2008; pp. 6170-6182; vol. 16; No. 9.

Johnson et al.; "Snapshot Hyperspectral Imaging in Ophthalmology"; Journal of Biomedical Optics; Jan./Feb. 2007; p. 014036-1-014036-7; vol. 12; No. 1.

Kong et al.; "Handheld Erythema and Bruise Detector"; Proc. of SPIE; pp. 69153K-1-69153K-7; vol. 6915, February.

Shonat et al.; "Near-Simultaneous Hemoglobin Saturation and Oxygen Tension Maps in Mouse Brain Using an AOTF Microscope"; Biophysical Journal; Sep. 1997; pp. 1223-1231; vol. 73.

Beach et al.; "Multi-Spectral Fundus Imaging for Early Detection of Diabetic Retinopathy"; SPIE; Jan. 1999; pp. 114-121; vol. 3603.

Hirohara et al.; "Validity of Retinal Oxygen Saturation Analysis: Hyperspectral Imaging in Visible Wavelength with Fundus Camera and Liquid Crystal Wavelength Tunable Fliter"; Optical Review; 2007; pp. 151-158; vol. 14; No. 3.

* cited by examiner

SNAPSHOT SPECTRAL IMAGING OF THE EYE

CROSS-REFERENCE TO RELATED APPLICATIONS

This application claims the benefit of the U.S. Provisional Application No. 61/064,420 filed on Mar. 5, 2008.

BACKGROUND OF THE INVENTION

1. Field of the Invention

This invention relates to spectral imaging, and more particularly, to a method and system for obtaining spectral images of retina.

2. Description of the Related Art

Spectral images are the images in which spectral information beyond the information that is required for producing a typical color image (that is typically based on the red, green, and blue components) is provided for every point of the image or pixel. This spectral information can be related to physiological properties of an object (e.g., physiological properties of the tissue as in retina being imaged) by choosing appropriate wavelength bands. Physiological properties can be related to different pathological conditions and can be further used clinically for diagnosis and for the indication of disease development. Therefore, the spectral images are especially useful because they incorporate physiological information together with anatomical and structural information.

A specific case in which spectral imaging is applicable is spectral imaging of the retina. Spectral imaging of the retina presents a unique opportunity for direct and quantitative mapping of retinal biochemistry. For example, blood oximetry is enabled by the strong variation of the hemoglobin absorption spectra with oxygenation. This is pertinent both to research and to clinical investigation and diagnosis of retinal diseases such as diabetic retinopathy, glaucoma, and age-related macular degeneration. These diseases are the major causes of blindness in the industrial world, in which their percentage is constantly growing as the result of environmental factors and the growth of life expectancy. In order to deal with these epidemic tendencies several screening programs have been started such as the UK National Screening Program.

The principle goal of such eye screening programs is the early detection of 'Diabetic Retinopathy,' wherein temporal retinal images of diabetic patients are obtained and sent for evaluation. The state of the retina is visually classified, and a referral is accordingly issued, inviting the patient to a specialist or scheduling the next retinal photography.

However, the applicability of these screening programs depends on minimizing the costs that are involved. The major contribution to these costs is the employment of professional people, especially medical doctors (MDs). For this reason, the programs are based on involving MDs only when necessary. Hence, the quality of the retinal images and the level of classification become crucial.

Further, in order to support efficient and cost-effective screening, different types of digital retinal cameras have been developed (e.g., CANON's CR-DGi and CR-1, Kowa's NONMYD7, Nidek's AFC-230/210, and Topcon's NW8.) The digital retinal cameras are designed to support efficient acquisition of retinal photographs by non-professional users and with minimal requirements on pupil dilation. Similarly, computer software has also been developed to support efficient and cost-effective networking and archiving of digital retinal photographs. However, classification of the images is performed manually, which is an intensive work and is subject to errors.

The optimal exploitation of spectral imaging of the eye presents a set of challenging problems, including the poorly characterized and poorly controlled optical environment of structures within the retina to be imaged; the erratic motion of the eyeball; and the compounding effects of the optical sensitivity of the retina and the low numerical aperture of the eye. Various systems have disclosed the basic science of spectral imaging (e.g., monitoring oxygen saturation levels by spectral imaging of the eye.) However, the conventional systems provide comparatively less sensitivity and specificity due to the time required to obtain enough spectral points to support reliable calculations. In addition, in order to eliminate the effect of eye movement, the typical speed for completing the measurement must be under 0.1 second, while the conventional systems typically require up to several seconds.

The first retinal imaging oximeter based upon photographic techniques was proposed by Hickam et al. in Circulation 27, page 375 (1963). This system disclosed a modified fundus camera that images the retina at two different wavelengths, filters the image from incandescent light sources, and extracts retinal blood vessels optical density with Beer-Lambert law. Measurements with this system have lead to inaccurate results because of the Beer-Lambert Law, which strictly limits two-wavelength oximetry only to hemolyzed solutions.

Pittman and Dulling in Applied Physiology 38, page 315 (1975), showed that more accurate results of retinal oximetry can be achieved using three wavelengths instead of two. This model took into account the scattering coefficient wavelength dependence.

Three-wavelength oximetry is based on several important principles. The first of these states that light absorption by blood depends on oxygen saturation (OS) and wavelength. Second, a relationship exists between a measurable optical quantity like optical densities and the extinction coefficient of the mixture of oxygenated hemoglobin ($HbO_2$) and deoxygenated hemoglobin (Hb) at a given OS as explained by van Assendelft in Spectrophotometry of hemoglobin derivatives (Springfield, Ill.: Thomas 1970), page 321. Finally, optical densities at two specific wavelengths can be compared to the optical density at a third specific wavelength; hemoglobin absorption values may then be calculated and be used to accurately obtain percent OS (Pittman and Duling in Applied Physiology 38, page 315 (1975)). The advantages and disadvantages of three wavelengths using existing technology have been explored by van Norren and Tiemeijer in Vision Res. 26, page 313 (1986) and by Delori and Pflibsen in Applied Optics 27, page 1113 (1988).

Three wavelength oximetry has been adapted for real-time measurements of retinal vessel OS as described by van Assendelft in Spectrophotometry of hemoglobin derivatives (Springfield, Ill.: Thomas 1970), page 321, and by Delori and Pflibsen in Applied Optics 27, page 1113 (1988). These retinal oximeters use a bright source of non-collimated light (such as a broad-spectrum halogen or arc lamps) that is filtered to provide three selected wavelengths. The light source and the filters are cooperatively selected to provide at least one isobestic wavelength (i.e., a wavelength at which hemoglobin absorption is essentially independent of OS) and at least one wavelength for which blood absorption is dependent upon OS. To probe a selected area of the retina, the light is focused on either a large caliber retinal artery or a large caliber retinal vein. The percent OS is calculated from measurements of the light reflected from either the artery (in which hemoglobin oxygenation is relatively high) or the vein (in which hemoglobin oxygenation is relatively low), and from the retinal pigment epithelium (RPE) background. However, this technique for performing retinal oximetry is complicated to control, requires precise focusing on retinal blood vessels and a complicated filtering system to produce a multi-wavelength probe. Thereby, it limits percent OS measurements to large caliber blood vessels and does not allow OS measurements to be made in the intra-retinal capillary beds.

In contrast to the above, "Full spectrum" methods (spectral methods that employ a large number of wavelengths values) have been used to record the reflectance profile versus wavelength from the ocular fundus. "Full spectrum" techniques use a high resolution imaging spectrograph to collect the spectral information from a band of tissue in a single spatial dimension. These spectrographs typically apply diffraction gratings and prisms in the spectral measurement of tunable wavelength. "Full spectrum" methods support the addition of parameters to the models that describe the spectral properties of the living (retinal) tissue, giving rise to more accurate estimates of OS in tissues outside large caliber blood vessels. Outside the large caliber vessels, the spectral signature of hemoglobin is less dominant than in the blood vessels. Examples can be found in F. C. Delori, "Reflectometry measurements of the optic disc blood volume," in Ocular Blood Flow in Glaucoma Means, Methods and Measurements, G. N. Lambrou, E. L. Greve eds., Berkely, Calif., Kugler and Ghedini, pp. 155-163 (1989); and F. C. Delori et al., "Spectral reflectance of the human ocular fundus," Appl. Optics, Vol. 28, pp. 1061-1077 (1989). In 1995, Schweitzer et al. [D. Schweitzer, M. Hammer, J. Kraft, E. Thamm, E. Koenigsdoerffer, and J. Strobel, "Calibration-free measurement of the oxygen saturation in retinal vessel of men," Proc. SPIE 2393, 210-218 (1995).] built an instrument that could image the retina spectroscopically with selecting light source wavelengths from 400 nm (15.75 micro inches) to 700 nm (27.56 micro inches) in 2 nm (0.07874 micro inch) intervals; an empirical scattering model was used in their calculations.

Gil et al. disclose in U.S. Pat. No. 6,276,798 a method and apparatus for spectral bio-imaging of the retina applying Fourier Transform to recover continuous spectra from interferograms that are obtained for each pixel by a Sagnac type interferometer. The interferometer is mounted on the video output of a fundus camera. Yoneya et al. have used such a system in various clinical studies, one of which is described in Ophthalmology 109(8), page 1521 (2002). The studies have shown that the clinical applicability of the technique is limited by the long acquisition time. Subsequently, the measured data contains noise and may not be accurate due to the movements of the eye during the acquisition.

Hirohara et al. in U.S. Patent Application No. 2007/0002276 and Mihashi et al. in U.S. Patent Application Nos. 2008/0007691 and 2008/0007692 disclose a spectroscopic fundus measuring apparatus that applies a liquid crystal tunable filter in combination with a spectral characteristic correction filter in order to select the transmission wavelength in the digital imaging system that is attached to a fundus camera. The filters are disposed either in the illumination optical system or in the light receiving system, and a special method is applied in order to shorten the wavelength shifting time upon the acquisition of the spectral image. The resulting acquisition time is still in the range of seconds. A method is provided to eliminate image position changes due to eye movements and a computer program is provided to align spectral images positions almost fully automatically.

Alabboud et al. in the Proceedings of SPIE, Volume 6631, and page 66310L (2007), describe a system comprising a liquid crystal tunable filter that is integrated into the illumination system of a conventional fundus camera to enable time-sequential, random access recording of narrow-band spectral images. Image processing techniques are used to eradicate the artifacts that may be introduced by time-sequential imaging.

Kagemann et al. in Society of Photo-Optical Instrumentation Engineer (2007) have used Fourier domain Optical Coherence Tomography (OCT) data to assess retinal blood oxygen saturation in three-dimensional disk-centered retinal tissue volumes. After removing DC and low-frequency a-scan components, an OCT fundus image is created by integrating total reflectance into a single reflectance value. Thirty fringe patterns are sampled, 10 each from the edge of an artery, adjacent tissue, and the edge of a vein, respectively. A-scans are recalculated, zeroing the DC term in the power spectrum, and used for analysis. Optical density ratios (ODRs) are calculated as ODRArt=ln(Tissue855/Art855)/ln(Tissue805/Art805) and ODRVein=ln(Tissue855/Vein855)/ln(Tissue805/Vein805) with Tissue, Art, and Vein representing total a-scan reflectance at the 805- or 855-nm (33.66 microinches) centered bandwidth. A difference between arterial and venous blood saturation was shown to be detected by this technique, suggesting that retinal oximetry may possibly be added as a metabolic measurement in structural imaging devices. However, this technology is yet to be developed completely.

In summary, all "Full spectrum" systems require an acquisition time during which the eye moves relative to the optical measuring system, giving rise to spectral distortion and patient discomfort. It is shown herein that these problems are resolved by the application of snapshot spectral imaging techniques, which remove the fundamental difficulties that are associated with time-sequential techniques.

Snapshot spectral imaging systems minimize or completely waive the problem with eye movements that distort the actual spectrum of the imaged object and aim at obtaining enough spectral information in a single exposure of the imaging detectors.

Hardarson et al. in Investigative Ophthalmology & Visual Science 47/11, page 5011 (2006), have used the MultiSpec Patho-Imager (Optical Insights, Tucson, Ariz.) on the video output of a fundus camera in order to obtain four images in four different wavelength bands on a single CCD detector array in one snapshot. Their studies show relative success in estimating OS in large retinal vessels but not in the surrounding retinal tissue. They conclude that improvement can be achieved with the incorporation of correction for additional tissue optical properties, which would require image data in more wavelength bands.

Ramella-Roman et al. in Optical Society of America 16/9, page 6170 (2008), describe a multi aperture system capable of capturing six identical images of the human fundus at six different spectral bands. The system is based on lenslet array architecture. The multi-aperture system is mounted on the image output of a fundus camera to acquire spectroscopic sensitive images of the retina vessel and ultimately to calculate OS in the retina in vivo. In vivo testing on healthy volunteers was conducted and yielded results of OS similar to the one reported in the literature, with arterial OS ~0.95 and venous OS ~0.5. The system suffers from several drawbacks. Among those is the need of registration among the six images that fall on the single image detector of the system. This need results from the specific properties of optical set up of the system. Additionally, a focusing screen that is used in the system in order to reduce the depth of field of the incorporated lenslets reduces the light intensity that eventually reaches the image detector, thus reducing the signal-to-noise ratio of the image. Finally, observing the spectral analysis of the results presented by Ramella-Roman et al. actually shows that the number of wavelength bands for every pixel in the image is still limiting fitting of OS model with measured data.

Johnson et al. in Journal of Biomedical Optics 12(1), 014036 (January/February 2007) describe the use of computed tomographic imaging spectrometer (CTIS) to perform snapshot hyper-spectral imaging of the eye. CTIS captures both spatial and spectral information in a single frame. Its acquisition time is constrained by the exposure time of the fundus camera on which the CTIS is mounted (typically about milliseconds) and a required signal-to-noise-ratio. It is capable of acquiring a complete spatial-spectral image cube in about 3 ms from 450 to 700 nm (17.72 to 27.56 microinches) with 50 bands, eliminating motion artifacts and pixel mis-registration. There are no narrow-band filters, and nearly all collected light (about 70%) is passed to the detector at all times. The CTIS is based on diffractive grating collimated in space and which disperses the image in two dimensions. A second lens re-images the pattern onto the image detector. This produces multiple, spectrally-dispersed, images of the retina that are recorded by a focal plane array (FPA). From the captured intensity pattern, computed-tomography algorithms are used to reconstruct the scene into a "cube" of spatial (x and y) and spectral (wavelength) information. Thus, each image is not simply composed of single wavelengths; spatial and spectral information from each object pixel is multiplexed over the entire detector array. Hence, a single acquisition contains all the information required to reconstruct the spectral image cube.

Initial results of studies on human healthy subjects show a clear distinction between veins, arteries, and background. Regions within vessel capillaries agree well with the 30 to 35% oxygen saturation difference expected for healthy veins and arteries. The saturation for most of the background spatial locations in between the capillary regions shows a tendency to be within the 90 to 100% regime. This is consistent with the subjects being healthy. As the CTIS records a multiple of spectrally-dispersed images on a single FPA, which is the detector array of a fundus camera, the genuine field of view (FOV) of the host fundus camera is reduced, typically by a factor of almost three. Accordingly, the maximal FOV of the CTIS is 18 degrees, corresponding to a 50 degrees fundus camera. Additionally, complicated calibration and extensive numerical approximations are required for recovering the spectral image, each contributing its error and SNR reduction as well as long processing time. CTIS is limited by inefficient usage of both the detector array and its large number of spectral bands when only a few are required.

Alabboud et al. in the proceedings of the SPIE, Volume 6631, and page 66310L (2007), describe a snapshot spectral imaging system and technique dubbed IRIS that employs polarizing interferometery and Wollaston prism beam splitters to simultaneously replicate and spectrally filter images of the retina into multiple spectral bands onto a single detector array. The system records eight images at eight different wavelength bands on a single photo-detector.

Results of early clinical trials acquired with IRIS together with a physical model, which enables oximetry map, were reported. However, the system as described yields a small field of view and gives rise to image intensity loss upon splitting the single-band images to their appropriate locations on the image detector. Additionally, it is based on a non-compact set that does not fit existing retinal imaging systems.

Kong et al. have used a method to develop a multispectral camera to acquire spectral images in a snapshot as described in Proc. SPIE 6915, 69153K (2008). They have used a multi-wavelength narrowband filter to replace the standard Bayer color filter on monochrome CMOS sensor of a digital camera, creating in this way a miniaturized multispectral imager. The device contains a mosaic filter for four wavelengths: 540, 577, 650, and 970 nm (38.19 microinches), with the purpose of detection of erythema and bruises in persons with darkly pigmented skin. In general term, this system is disclosed in the International Patent Application PCT/US2007/087479.

In light of the above discussion, there is a need for a method and system that provides automatic classification of diabetic retinopathy. In addition, there is a need for a method and system that may significantly affect the efficiency and cost-effectiveness of screening techniques. Further, there is a need for a method and system that enables obtaining spectral images of the retina by the aforementioned non-mydriatic retinal cameras after fitting them with already modified camera-backs. Still further, such a method and system may utilize algorithms that apply the spectral information to estimate blood hemoglobin oxygen saturation in each point of the images for automatic classification of the progress of retinal vascular diseases such as diabetic retinopathy.

Accordingly, it is an object of the invention to provide an improved method and system for spectral imaging of the eye that provides spectral points (wavelength bands) to deal with the poorly characterized and poorly controlled optical environment of structures within the retina under the compounding effects of the optical sensitivity of the retina and the low numerical aperture of the eye; without registration and spectral distortion problems that are associated with time-sequential techniques because of the erratic motion of the eye ball; and without the complexity, small field of view, and intensity loss that characterize current snapshot techniques.

SUMMARY OF THE INVENTION

Various embodiments of the present invention disclose a method and system for spectral imaging of the eye. In accordance with an embodiment of the present invention, a filter array fitted to the detector array of a digital imaging system may be disclosed. Currently, a color filter array (CFA) is used in the image sensor to separate different color photons in incident light. An example may be of a color filter array having a Bayer filter pattern that is placed in front of the pixel array to obtain the color information of the optical image. In a Bayer filter pattern CFA, the color filters are quartet-ordered with successive rows that alternate red and green filters, then green and blue filters. Each of the color filters is sensitive to one color and allows photons of that color to pass through and reach the corresponding photo-sensor. The photo-sensor in each pixel thereby detects and measures only the light of the color associated with the filter provided within that pixel. There are various other color filter arrays formed with alternative filter patterns, such as a CYMG (cyan, yellow, magenta, green) filter pattern, a CKMY (cyan, black, magenta, yellow) filter pattern, an RGBE (red, green blue, emerald) filter pattern, and other patterns having red, green, and blue filters and another color filter arranged between green and blue filters, and others.

The CFA technology has been widely used in the digital camera industry since it provides several advantages like low cost, exact registration, and strong robustness. The idea of CFA has also been extended to multi-spectral filter array (MSFA). In MSFA more than three color bands are used (e.g. visible and infrared). Moreover, when dealing with retinal imaging, the resolution of SLR camera backs is much higher than the intrinsic resolution of the human eye optics; accordingly, it is shown in the description of this invention below that it is possible to increase (more than triple) the number of spectral bands without reducing the effective resolution of the system.

In accordance with an embodiment of the present invention, as embodied and broadly described herein, a method may be provided for reforming digital instruments that are used for imaging the human eye, e.g., digital ophthalmoscopes, fundus cameras, slit lamps, and operation microscopes into spectral imaging systems by fitting a MSFA to their imaging sensors.

In accordance with another embodiment of the present invention, non-mydriatic fundus cameras may be reformed into non-mydriatic retinal spectral imaging systems by fitting an MSFA to the image detector array of the digital SLR camera back of the fundus camera.

In an embodiment of the present invention, MFSA may be optically fitted to a bare (Black and White) digital imaging detector array of a fundus camera, comprising a set of filters of wavelength bands that may be suitable for retinal oximetry when multiplied by the spectral response of the detector array.

In another embodiment of the present invention, MFSA may be optically fitted to a detector array of a color camera that is already covered with a Bayer RGB filter array, comprising another set of filters of wavelength bands that are suitable for retinal oximetry when multiplied by the spectral response of the detector array and the RGB spectra.

In yet another embodiment of the present invention, MFSA may be optically fitted to a detector array of a color camera that is already covered with a CMYG (cyan, yellow, magenta, green) filter array, comprising yet another set of filters of wavelength bands that are suitable for retinal oximetry when multiplied by the spectral response of the detector array and the CYMG spectra.

In an aspect of the invention, methods and systems for obtaining spectral images of an eye include taking an optical system that images eye tissue onto a digital sensor array; providing a multi-spectral filter array; optically fitting the multi-spectral filter array and the digital sensor array, wherein the multi-spectral filter array is disposed between the digital sensor array and an optics portion of the optical system; and facilitating acquisition of a snap-shot image of the eye tissue with the digital sensor array.

In the aspect, the multi-spectral filter array comprises at least nine different spectral bands. At least one of the spectral bands is centered at a wavelength selected from the group consisting of values of 522, 532, 542, 549, 555, 569, 577, 586, and 600 nm wavelengths. Alternatively, at least one of the spectral bands is centered at a wavelength selected from the group consisting of values of 430, 449, 522, 532, 542, 549, 555, 569, 577, 586, 600, and 650 nm wavelengths. In the aspect, the spectral bands are designed to support estimation of blood oxygen saturation in a retinal tissue.

In the aspect, the optical system is a fundus camera. The optical system is designed to obtain retinal images. Alternatively, the optical system is a non-mydriatic fundus camera designed to obtain the retinal images without administration of pupil dilation drops. The optical system may be a slit lamp instrument. The optical system may include an illumination source selected from a set consisting of a halogen lamp, a xenon lamp, metal halide lamp, light emitting diodes (LED), laser diodes, solid state laser, and flash lamps In the aspect, the multi-spectral filter array comprises a plurality of filter elements each of which is optically associated with an integer number of detectors of the digital sensor array.

In the aspect, optically fitting includes depositing the multi-spectral filter array on a light sensing surface of the sensor array. Alternatively, optically fitting includes depositing the multi-spectral filter array on a cover glass attached to a light sensing surface of the sensor array. Optically fitting may also include depositing the multi-spectral filter array on a thin film attached to a light sensing surface of the sensor array.

In the aspect, the methods and systems may include a micro-lenses array attached to the multi-spectral filter array for limiting an angle of light that is transmitted through the multi-spectral filter array.

In the aspect, the methods and systems may include a micro-pinhole array attached to the multi-spectral filter array for limiting an angle of light that is transmitted through the multi-spectral filter array.

In the aspect, the multi-spectral filter array is divided into unit cells each comprising multi-spectral filters. Each unit cell comprises at least nine filters of nine different spectral bands.

In the aspect, the sensor array lies inside a detachable camera back of the optical system. The sensor array is a grey level sensor array or a color-coated sensor array.

In the aspect, the long axis of the image of the eye tissue falls on at least 2592 pixels of the sensor array.

In another aspect of the invention, methods and systems of facilitating obtaining spectral images of an eye include taking an optical system that images eye tissue onto a digital sensor array and optically fitting a multi-spectral filter array with the digital sensor array so that light for imaging the eye tissue that reaches the digital sensor array is filtered by the multi-spectral filter array.

In the aspect, the multi-spectral filter array comprises at least nine different spectral bands. At least one of the spectral bands is centered at a wavelength selected from the group consisting of values of 522, 532, 542, 549, 555, 569, 577, 586, and 600 nm wavelengths. Alternatively, at least one of the spectral bands is centered at a wavelength selected from the group consisting of values of 430, 449, 522, 532, 542, 549, 555, 569, 577, 586, 600, and 650 nm wavelengths. In the aspect, the spectral bands are designed to support estimation of blood oxygen saturation in a retinal tissue.

In the aspect, the optical system is a fundus camera. The optical system is designed to obtain retinal images. Alternatively, the optical system is a non-mydriatic fundus camera designed to obtain the retinal images without administration of pupil dilation drops. The optical system may be a slit lamp instrument. The optical system may include an illumination source selected from a set consisting of a halogen lamp, a xenon lamp, metal halide lamp, light emitting diodes (LED), laser diodes, solid state laser, and flash lamps In the aspect, the multi-spectral filter array comprises a plurality of filter elements each of which is optically associated with an integer number of detectors of the digital sensor array.

In the aspect, optically fitting includes depositing the multi-spectral filter array on a light sensing surface of the sensor array. Alternatively, optically fitting includes depositing the multi-spectral filter array on a cover glass attached to a light sensing surface of the sensor array. Optically fitting may also include depositing the multi-spectral filter array on a thin film attached to a light sensing surface of the sensor array.

In the aspect, the methods and systems may include a micro-lenses array attached to the multi-spectral filter array for limiting an angle of light that is transmitted through the multi-spectral filter array.

In the aspect, the methods and systems may include a micro-pinhole array attached to the multi-spectral filter array for limiting an angle of light that is transmitted through the multi-spectral filter array.

In the aspect, the multi-spectral filter array is divided into unit cells each comprising multi-spectral filters. Each unit cell comprises at least nine filters of nine different spectral bands.

In the aspect, the sensor array lies inside a detachable camera back of the optical system. The sensor array is a grey level sensor array or a color-coated sensor array.

In the aspect, the long axis of the image of the eye tissue falls on at least 2592 pixels of the sensor array.

In yet another aspect of the system, methods and systems of eye spectral imaging include an optical system that images eye tissue onto a digital sensor array and a multi-spectral filter array that is optically fitted with the digital sensor array, wherein the multi-spectral filter array is disposed in close proximity to the digital sensor array in the optical path of the optical system.

In the aspect, the multi-spectral filter array comprises at least nine different spectral bands. At least one of the spectral bands is centered at a wavelength selected from the group consisting of values of 522, 532, 542, 549, 555, 569, 577, 586, and 600 nm wavelengths. Alternatively, at least one of the spectral bands is centered at a wavelength selected from the group consisting of values of 430, 449, 522, 532, 542, 549, 555, 569, 577, 586, 600, and 650 nm wavelengths. In the aspect, the spectral bands are designed to support estimation of blood oxygen saturation in a retinal tissue.

In the aspect, the optical system is a fundus camera. The optical system is designed to obtain retinal images. Alternatively, the optical system is a non-mydriatic fundus camera designed to obtain the retinal images without administration of pupil dilation drops. The optical system may be a slit lamp instrument. The optical system may include an illumination source selected from a set consisting of a halogen lamp, a xenon lamp, metal halide lamp, light emitting diodes (LED), laser diodes, solid state laser, and flash lamps In the aspect, the multi-spectral filter array comprises a plurality of filter elements each of which is optically associated with an integer number of detectors of the digital sensor array.

In the aspect, optically fitting includes depositing the multi-spectral filter array on a light sensing surface of the sensor array. Alternatively, optically fitting includes depositing the multi-spectral filter array on a cover glass attached to a light sensing surface of the sensor array. Optically fitting may also include depositing the multi-spectral filter array on a thin film attached to a light sensing surface of the sensor array.

In another aspect of the invention, the methods and systems may include a micro-lenses array attached to the multi-spectral filter array for limiting an angle of light that is transmitted through the multi-spectral filter array.

In yet another aspect of the invention, the methods and systems may include a micro-pinhole array attached to the multi-spectral filter array for limiting an angle of light that is transmitted through the multi-spectral filter array.

In the aspect, the multi-spectral filter array is divided into unit cells each comprising multi-spectral filters. Each unit cell comprises at least nine filters of nine different spectral bands.

In the aspect, the sensor array lies inside a detachable camera back of the optical system. The sensor array is a grey level sensor array or a color-coated sensor array.

In the aspect, the long axis of the image of the eye tissue falls on at least 2592 pixels of the sensor array.

In another aspect, the methods and systems include a computer capable of reconstructing the spectral images. The computer includes a program capable of analyzing the spectral images. Reconstructing the spectral images includes de-mosaicking of spectral data from readings of the digital sensor array.

These and other systems, methods, objects, features, and advantages of the present invention will be apparent to those skilled in the art from the following detailed description of, the preferred embodiment and the drawings. All documents mentioned herein are hereby incorporated in their entirety by reference.

BRIEF DESCRIPTION OF THE DRAWINGS

The invention and the following detailed description of certain embodiments thereof may be understood by reference to the following figures:

FIG. 2 depicts a graphic illustration of the arrangement of spectral band filters in the filter array of the principle embodiment of the invention;

FIG. 6 depicts an arrangement of spectral bands on top of a CYMG-coated quadratic imaging detector array in order to realize an embodiment of the invention.

DETAILED DESCRIPTION OF THE PREFERRED EMBODIMENT(S)

Throughout this disclosure, the phrase "such as" means "such as and without limitation". Throughout this disclosure, the phrase "for example" means "for example and without limitation". Throughout this disclosure, the phrase "in an example" means "in an example and without limitation". Throughout this disclosure, the phrase "in another example" means "in another example and without limitation". Generally, examples have been provided for the purpose of illustration and not limitation.

Figure 1:
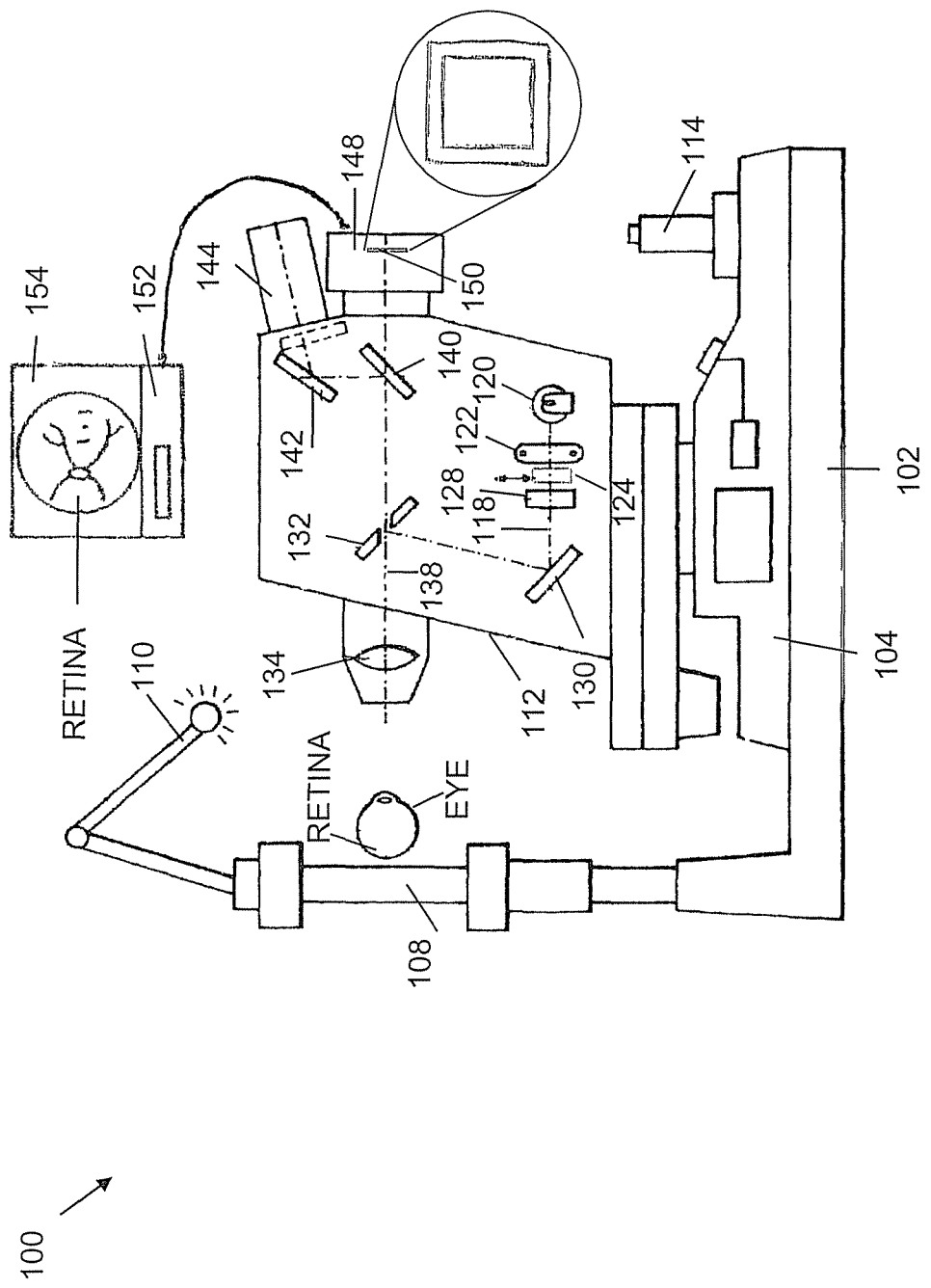
FIG. 1 depicts a schematic view of a fundus camera with an exchangeable digital camera back.

FIG. 1 depicts the principle elements of a typical eye fundus camera 100 with a digital camera back 148, in accordance with an embodiment of the present invention. The camera 100 is described here in general only in order to better clarify the embodiments of this invention. A chin rest face holder 108 is an extension of camera base 102 and may include an eye fixation lamp 110. A joystick-adjustable stage 114 may be placed on top of the camera base 102 that holds the optical system or unit 112. By use of joystick 114, stage 104 may be moved back and forth, right and left, and optical unit 112 may be moved up and down in order to bring the optical unit 112 into correct optical contact with the eye element that is imaged. The optics of the fundus camera 100 can be divided into illumination optics and imaging optics. The illumination optics may consist of a flash lamp 120, such as xenon lamp, continuous illumination source 122, such as halogen lamp, exchangeable filter 124, pupil 128, folding mirror 130, perforated mirror 132, and objective lens 134. The imaging optics may comprise an objective lens, beam splitter 140, digital camera back 148, with digital detector array 150 (CCD or CMOS that is illustrated in the round blowup), flipping mirror 142, and eyepiece 144. Digital camera 100 may be connected to computer 152 with display 154, into which the digital image is downloaded.

The process of acquiring an image of an eye part, e.g., the retina, may start with dilating the eye pupil of the patient with mydriatic drops in order to keep the pupil dilated all through the photography process, allowing enough light in and out of the eye. The patient may then rest the head on the chin rest face holder 108 so that the eye is relatively fixed in space. This may follow with an alignment process in which the eye is illuminated by illumination beam 118, originating from the continuous light source 122. Reflection light beam 138 may be directed to eyepiece 144, with flipping mirror 142 in the appropriate position, allowing the operator to see the image of the retina and aligning optical unit 112 by aid of joystick 114 until an optimal image is obtained. At this point an image may be recorded by pressing the electric trigger on joystick 114, activating flash lamp 120 and the digital image detector 150. In a non-mydriatic fundus camera eyepiece 144 may be replaced by a digital alignment system with a monitor display that provides graphical alignment aids and may typically operate under near-infrared (NIR) illumination that is obtained with an appropriate light source 122 and filter 124. Under NIR illumination, the eye pupil may remain dilated, allowing enough light in and out of the eye, contracting in delay to the aforementioned flash, thus allowing image acquisition without mydriatic dilation drops. The maximal Field of View (FOV) of typical non-mydriatic cameras is 45 degrees, such that in its long axis the retinal image covers approximately 8.64 mm (approximately 0.3402 inch).

In accordance with an embodiment of the present invention, a multi-spectral filters array may be optically fitted or directly deposited onto an imaging detector array 150 of a digital fundus camera 100, thus producing snapshot spectral images of the retina. This has been illustrated in FIG. 2 that describes a square detector array, wherein every square denotes a detection subunit (pixel).

Figure 2:
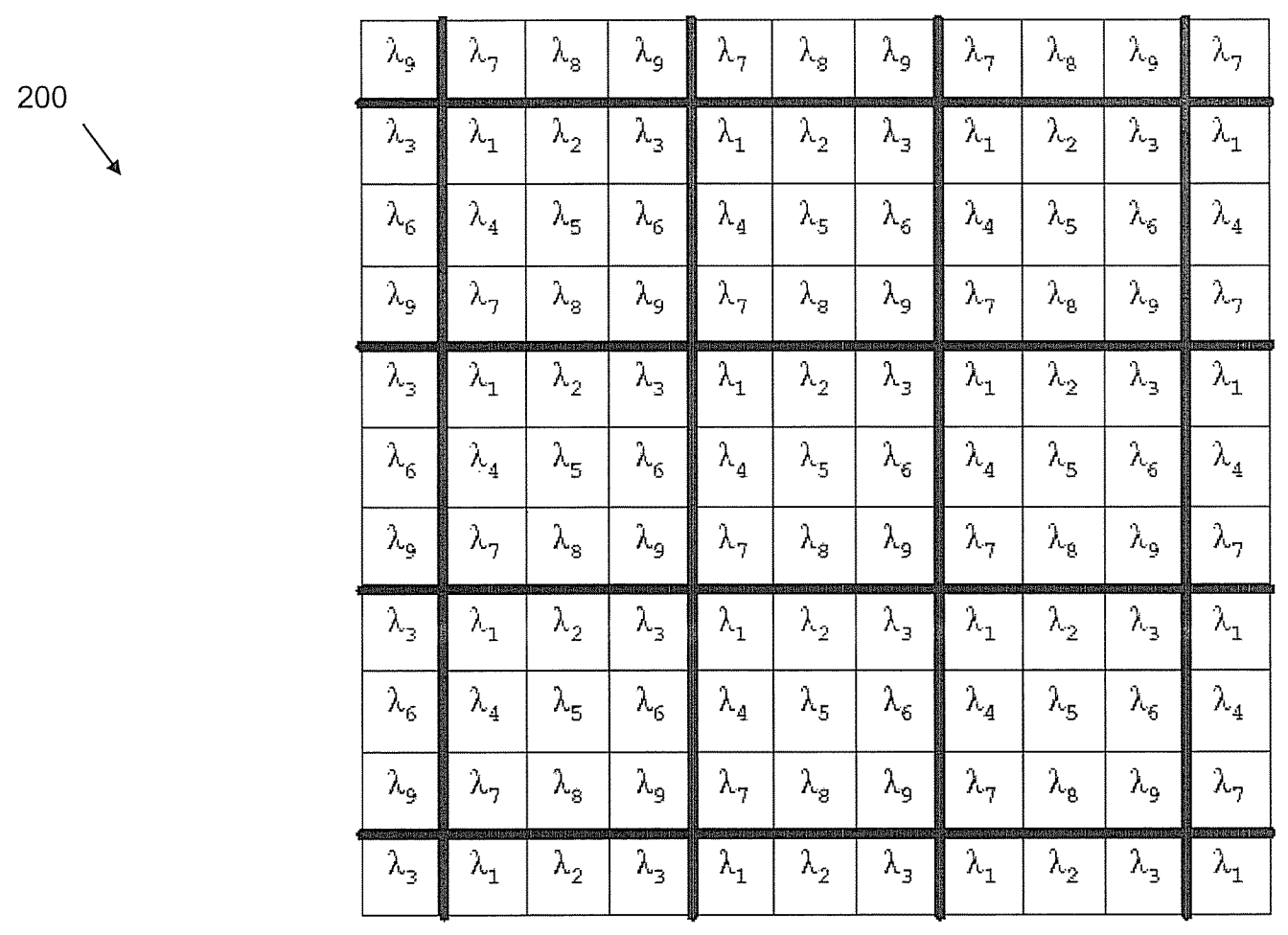

Referring to FIG. 2, a square detector array optically fitted with a corresponding filter array may be described such that each detector unit (pixel) is covered by one filter unit that is denoted by $\lambda i$, where 'i' is an index that goes from one to N. N denotes the number of different wavelength bands that are defined in the array. In accordance with a preferred embodiment, $\lambda i$ may be the central wavelength of the spectral response that results from the combination (product) of the spectral response of the detector and the spectral response of the attached filter.

The arrangement of the filters may be periodic and may be divided into unit cells. Each unit cell may consist of exactly N different filters and the position of each $\lambda i$ filter within the cell may be indicated by the (m,n), where m=1 ... $\sqrt{N}$ and n=1 ... $\sqrt{N}$, respectively. The size of a unit cell may be $(l \times \sqrt{N})$ 2, where l is the length of each quadratic pixel of the detectors array. A meaningful spectral image may be constructed when the optical set up is such that a unit cell images a portion of the object that is spectrally homogeneous from the applicative point of view. Hence, when acquiring an image through the filters array of FIG. 2, a spectrum consisting of N=9 central wavelength points may be reconstructed. When dealing with imaging the retina, it is generally accepted that the resolving limit of the human eye are 10 microns (393.7 microinches) on the retina. The requirement from the spatial resolution of the spectral imaging system may accordingly determine so that every $\sqrt{N}$ pixels would image 10 microns (393.7 microinches) of the retina. In a preferred case wherein the retinal camera is a non-mydriatic fundus camera of a 45 degrees FOV and the image on the long axis covers an arc of retina of approximately 8.64 mm, it may be required that detector array 150 in FIG. 1 comprise at least $864 \times \sqrt{N}$ pixels on the long axis.

For example, Canon's CR-DGi 45 degrees non-mydriatic fundus camera fitted with an EOS-1DS Mark II SLR camera back of 16.7 million pixels and 4992 pixels on the long axis. $\sqrt{N}$ that would satisfy the aforementioned requirement will be five, implying 25 spectral points for every 10×10 square microns on the retina.

Certain unpublished experiments have shown that the minimal value of N that is required for correctly recovering the spectrum of oxygenated and non-oxygenated hemoglobin in arterial and venous human blood is nine. Therefore, N=9 would mean that sensor arrays with at least $864 \times \sqrt{N} = 2592$ pixels on the long axis would yield a spectral image with a spatial resolution matching the resolution of the human eye. Typical digital cameras of 5 million pixels would already satisfy this requirement. Moreover, this requirement is satisfied even on the short axis of Kowa's NONMYD 7 and Topcon's TRC-NW8 when applying NIKON's D80 camera back with 10 million pixels of 3872 pixels on the long axis and 2592 pixels on the short axis. The aforementioned CANON's CR-DGi 45 degrees non-mydriatic fundus camera with the EOS-1DS Mark II SLR camera back will be resolving 5.19 microns (204.3 microinches) on the retina with N=9, which is beyond the resolution of a typical human eye optics.

A specific application of retinal spectral imaging may be the estimate of oxygen saturation levels over the entire imaged retina, including vessels and retinal tissue. With N=9 a representative spectra that would distinguish clearly between oxygenated and non-oxygenated hemoglobin can be reconstructed from spectral bands of full-width-half-maximum (FWHM) of 15 nm (0.5906 micro inch) that are centered at $\lambda 1, \ldots, 9 = 522, 532, 542, 549, 555, 569, 577, 586, 600$ nm, respectively. These wavelengths are only representative of one embodiment. Other wavelengths may provide usable results and are incorporated herein. In one example, shifting each wavelength up to 20 nm may provide usable results.

Figure 3:
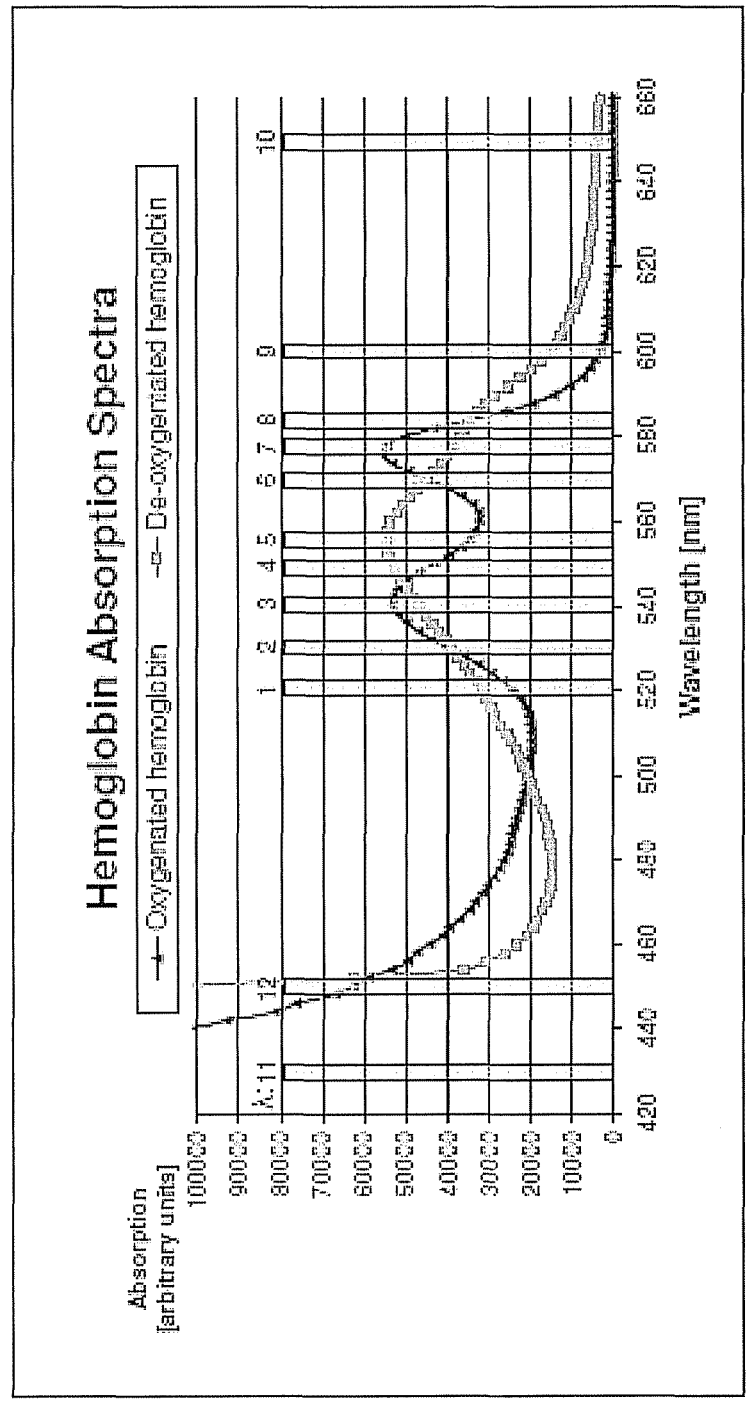
FIG. 3 depicts the position of chosen central wavelength values on top of hemoglobin absorption spectra.

FIG. 3 depicts the central spectral position of these wavelength bands relative to the absorption spectra of oxygenated and de-oxygenated hemoglobin. Small corrections to these values may be required when adapting to the specific spectral response of a chosen detectors array.

In the periodic arrangement of FIG. 2, denoting the position of $\lambda i$ by $(m_i, n_i)$ it may be observed that the spectral bands positioned at $(m_i, n_i)$ are equal for all the unit cells. For example $\lambda 7$ is always positioned (3,1). Accordingly, the reconstruction of the spectrum attributed for each unit cell from the intensities recorded on each pixel of the arrays of the detectors may be easily done in a straightforward manner. Alternatively, more sophisticated methods and algorithms can be applied in reconstructing the spectral image, among which are methods in which each pixel is attributed the full spectrum by interpolation on the intensity values recorded at nearest-neighbor pixels of equal spectral band. In general, different de-mosaicking techniques as described herein and elsewhere may be used to optimize the retrieving of the spectral image from the readings of the detectors array, some useful de-mosaicking techniques are known to those skilled in the art.

Once a spectrum is attributed, every unit cell, or every pixel in the case where an interpolation technique is used, may be analyzed in order to provide physiological or chemical information related to the imaged object at the location that is imaged by the respective unit cell, or pixel, In accordance with an embodiment of the present invention, the methods and systems described herein may be used to obtain a spectrum that may be used to estimate oxygen saturation using various techniques. A spectrum obtained by the methods and systems herein may work well with the estimation technique suggested by Shonat et al. in Biophysical Journal 73, page 1223 (1997). Various analysis techniques of a spectrum that may be obtained by the methods and systems described herein has been discussed in numerous papers (see for example Schweitzer et al. in SPIE 2393, page 210 (1995), Beach et al. in SPIE (1998) and U.S. Pat. No. 6,276,798). Therefore, the methods and systems described herein provide immediate benefit to currently used analysis techniques.

In an aspect of the present invention, grey levels (Black and White) image detector 150 (FIG. 1) may be used. In alternative embodiment of the present invention desired spectral bands may be obtained by fitting a filter array to detector arrays of commercially-available color digital cameras, e.g., RGB (red, green, and blue)-coated and CYMG (cyan, yellow, magenta, green)-coated arrays.

Figure 4:
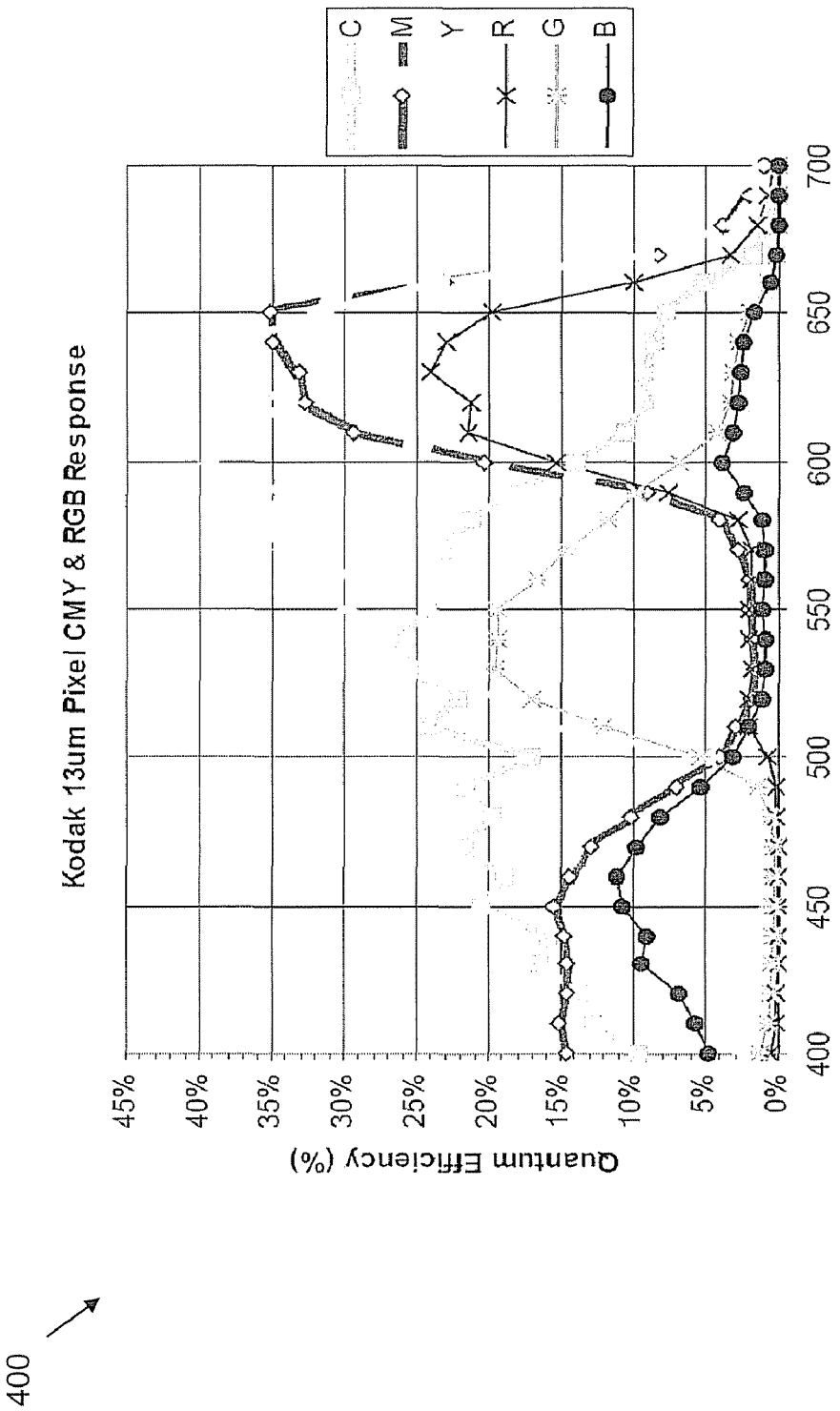
FIG. 4 depicts the spectra of RGB and CYMG-coated detector arrays.

FIG. 4 depicts the spectrum of each one of these colors, in accordance with an embodiment of the present invention. The filters in the corresponding arrays may be then designed in a way that their combination (product of spectra) with the existing CFA pattern yields the desired spectral bands.

Figure 5:
FIG. 5 depicts an arrangement of spectral bands on top of an RGB-coated quadratic imaging detector array in order to realize an embodiment of the invention.

FIG. 5 shows wavelength bands when the imaging detector array is already covered with a quadratic BAYER RGB pattern, in accordance with another embodiment of the present invention. The BAYER RGB pattern unit cell consists of four pixels, two of which are green-coated (G), one is red-coated (R), and the last one is blue-coated (B) as denoted by the R, G, and B letters in FIG. 5. The filter array may be optically fitted on the RGB detector array and may have 4×4-unit cell as illustrated by the thick solid lines in FIG. 5. Each filter may comprise nine wavelength bands, denoted by $\lambda 11,12,2,3,5,7, 8,9,10\ldots,9=430, 449, 532, 542, 555, 577, 586, 600, 650$ nm, respectively, and described accordingly in FIG. 3.

According to the aforementioned calculation, the number of pixels that may be required in this case in order to comply with the maximal spatial resolution (determined by the resolution of the typical eye optic) would be at least $(864\times\sqrt{N}=)$ 3456 pixels on the long axis, for N=16. It may be observed that this requirement is fulfilled by the aforementioned SLR camera backs.

Figure 6:
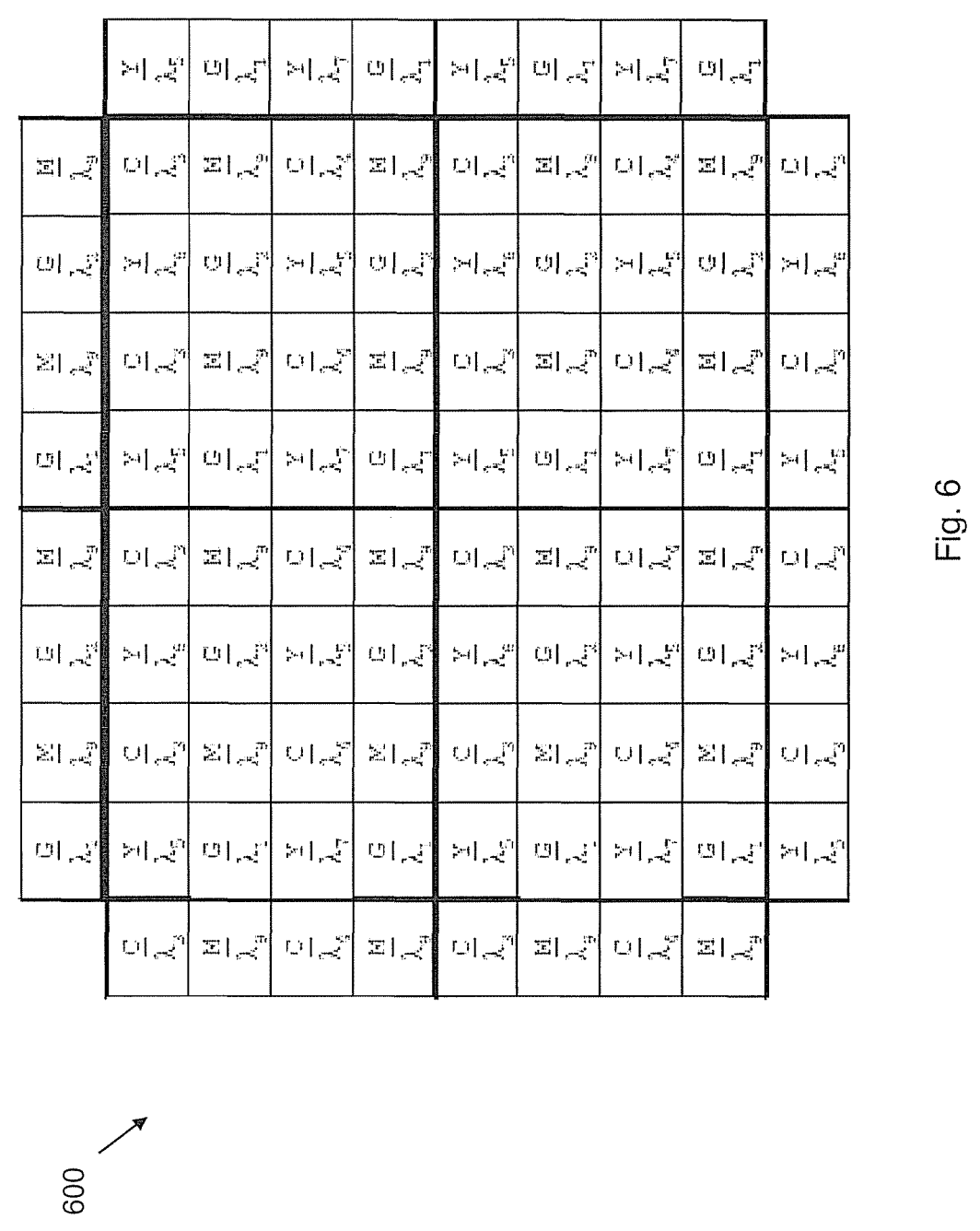

FIG. 6 depicts wavelength bands for the case in which the imaging detector array is already covered with a quadratic CYMG pattern, in accordance with an embodiment of the present invention. The CYMG pattern unit cell consists of four pixels, one for each color as denoted by the letter C, Y, M, and G, in FIG. 6. The filter array may be optically fitted on the CYMG detector array and may have accordingly a 4×4 unit cell as illustrated by the thick solid lines in FIG. 6. Each filter comprises 9 wavelength bands, denoted by $\lambda 1, \ldots, 9=522, 532, 542, 549, 555, 569, 577, 586, 600$ nm and described accordingly in FIG. 3.

According to the aforementioned calculation, the number of pixels that would be required in this case in order to comply with the maximal spatial resolution that is determined by the resolution of the typical eye optic would be at least $(864\times \sqrt{N}=)3456$ pixels on the long axis, for N=16.

It may be noted that in the embodiments of FIGS. 5 and 6, it may be in principle possible to apply 16 wavelength bands. This may become necessary, depending on the application of the spectral imaging system. Additionally, it may be noted that in FIGS. 5 and 6, all nine wavelength bands may be found in "rolling" 3×3 unit cells supporting spectral interpolation algorithms that may increase the effective spatial resolution of a resulting spectral image.

Referring to FIG. 3, the isosbestic points of oxygenated and de-oxygenated hemoglobin spectra are at 522, 549, 569, and 586 nm. At the isosbestic wavelengths the extinction coefficients of both oxygenated and non-oxygenated hemoglobin may be equal. The oxygenated hemoglobin (HbO2) maxima are at 542 and 577 nm; and the non-oxygenated hemoglobin (Hbr) maximum is at 555 nm. Therefore, the aforementioned choice of spectral bands may be optimal for reconstructing the hemoglobin spectrum. Interference filters with these characteristics may be found off-shelf, and various companies offer the capability of creating such dielectric dichroic (interference) filter arrays on thin films in the dimensions that match the sizes and shapes that are depicted in the embodiments of this invention. In the case of an interference filter array a micro lens array may be added in order to control the angular content of the beam reaching each one of the filters in the array because the performance of interference filters depends on the angle of the incident light. This angle may also be controlled by an array of micro-pinholes that would be attached to the filter array so that a micro-pinhole is centered in front of every filter in the array.

One process combines modern optical thin film deposition techniques with microlithographic procedures. This process enables micron-scale precision patterning of optical thin film dichroic coatings on a single substrate. A dichroic filter may selectively transmit light according to its wavelength. With its process, Ocean Optics can create multi-patterned arrays of different optical filters. The process may also be applied to CCD camera detectors. Since, this process relies on precision microlithography instead of cut metal masks to pattern the deposited coatings, features (coated areas) as small as 2 μm can be produced, with spatial registration to within 1 μm. The cost of microlithographic tooling does not increase significantly with pattern complexity.

Similarly, another process discloses a resist lift-off technique for applying patterned multispectral coatings on a single substrate or, for some cases, directly on the surface of a CCD. This technique has been applied successfully at DSI since the early nineties. The coatings can have micron-scale features, consist of as many as 100 coating layers, and meet stringent environmental and durability standards. Production of multispectral filters using resist lift-off starts with a bare, clean substrate. The substrate is then treated with an adhesion promoter, which helps the photoresist adhere to the substrate. After the adhesion promoter, positive photoresist is applied. The next step, following proper application of the photoresist, is exposure. Once the desired area has been exposed, the resist from the exposed area is removed. This is accomplished during the development step of the process. The substrates with the patterned photoresist masks are then placed in a vacuum coating chamber where controlled deposition of the desired coating is accomplished. After deposition, the coated substrate is submerged in solvent, which dissolves the photoresist, allowing the coating on top of the photoresist to be washed away and leaving the desired patterned coating. This procedure is repeated to construct multiple filters on the same substrate.

In accordance with various embodiments of the present invention, a non-mydriatic digital retinal camera (that acquires snapshot color images of the retina through a minimally and spontaneously dilated pupil) may be turned into a snapshot spectral imaging system by fitting a filters array to its sensors array. The suggested spectral bands together with an appropriate de-mosaicking technique and software analysis may yield estimation of oxygen saturation levels across the imaged retina. Oxygen saturation maps can serve for diagnosis of retinal vascular diseases and for automatic classifications of these diseases in general. Consequently, the efficiency of eye screening programs may be improved.

CFA-based color digital cameras have been incorporated either internally into eye imaging systems or as an add-on and exchangeable component. The latter approach has not been abandoned although all new instruments are designed digital from the start because the speed in which new sensor arrays and camera backs are appearing in the market, offering constant improvement in spatial and spectral resolutions, sensitivity, speed of acquisition, color accuracy, etc. The present invention can follow up on these commercial trends and fit appropriate filter arrays to newly appearing camera backs, enhancing the applicability of corresponding imaging systems.

The invented system deals with all the problems that have prevented the commercialization of a retinal oximeter until this day, i.e., eye movements, the number of spectral bands that compose the reconstructed spectrum, image resolution, manufacturability, and cost-efficiency.

In accordance with the embodiments of the present invention illustrated in FIGS. 2, 5, and 6, a rectangular array of light-sensing elements may be used. However, the present invention is not restricted to this arrangement and can be applied to any tessellation geometry as long as the single pixel size is within the range that allows the narrow band filters adaptation. Similarly, sensors of new shapes other than rectangular and new sampling schemes other than rectangular sampling may be used in order to optimize resolution over a given sensors array total size without reducing the active area of the individual sensor.

Various embodiments of the present invention provide unique advantages over existing or conventional multi-spectral alternatives in terms of image registration, calibration, light transmission, cost, physical size, and mechanical robustness.

Embodiments of the present invention, in particular, for retinal spectral imaging, allow a large number of spectral points in a snapshot to a level that is not possible applying other aforementioned technologies and systems.

Moreover, when applied to non-mydriatic retinal cameras, the present invention paves the way to automatic disease classification upon eyes screening, e.g., in the case of diabetic patients.

Beyond spectral imaging of the retina, the present invention is applicable to spectral tissue imaging in general and to any other application that apply digital cameras of a resolution that is high enough relative to spectral variations along the imaged objects. For example, this method could also measure OS from other tissues that reflect light sufficient to give a clear spectra from the blood hemoglobin, e.g., skin, tongue, and/or intestine.

It may be understood that the description is not meant as a limitation, since further modifications may now suggest themselves to those skilled in the art, and it is intended to cover such modifications as fall within the scope of the appended claims. Moreover, similar techniques could be applied for spectral imaging in general and additional clinical applications in particular, e.g., the viability of tissue undergoing transplantation, skin graft, free flap, etc.

The methods and systems described herein may be deployed in part or in whole through a machine that executes computer software, program codes, and/or instructions on a processor. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipments, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference.

The invention claimed is:

1. A method for obtaining spectral images of an eye, comprising:
    taking an optical system that images eye tissue onto a digital sensor array;
    providing a multi-spectral filter array;
    optically fitting the multi-spectral filter array and the digital sensor array, wherein the multi-spectral filter array is disposed between the digital sensor array and an optics portion of the optical system and comprises a plurality of filter elements each of which is optically associated with an integer number of detectors of the digital sensor array; and
    facilitating acquisition of a snap-shot image of the eye tissue with the digital sensor array.

2. A method of facilitating obtaining spectral images of an eye, comprising:
    taking an optical system that images eye tissue onto a digital sensor array; and
    optically fitting a multi-spectral filter array with the digital sensor array so that light for imaging the eye tissue that reaches the digital sensor array is filtered by the multi-spectral filter array,
    wherein the multi-spectral filter array comprises a plurality of filter elements each of which is optically associated with an integer number of detectors of the digital sensor array.

3. A system of eye spectral imaging comprising:
    an optical system that images eye tissue onto a digital sensor array; and
    a multi-spectral filter array that is optically fitted with the digital sensor array, wherein the multi-spectral filter array is disposed in close proximity to the digital sensor array in the optical path of the optical system and comprises a plurality of filter elements each of which is optically associated with an integer number of detectors of the digital sensor array.

4. The system of claim 3, wherein the multi-spectral filter array comprises at least nine different spectral bands.

5. The system of claim 4, wherein the spectral bands are designed to support estimation of blood oxygen saturation in a retinal tissue.

6. The system of claim 3, wherein the optical system is a fundus camera.

7. The system of claim 3, wherein the optical system is a non-mydriatic fundus camera designed to obtain the retinal images without administration of pupil dilation drops.

8. The system of claim 3, wherein optically fitted includes deposited on a light sensing surface of the sensor array.

9. The system of claim 3, wherein optically fitted includes deposited on a cover glass attached to a light sensing surface of the sensor array.

10. The system of claim 3, wherein optically fitted includes deposited on a thin film attached to a light sensing surface of the sensor array.

11. The system of claim 3, further comprising a microlenses array attached to the multi-spectral filter array for limiting an angle of light that is transmitted through the multi-spectral filter array.

12. The system of claim 3, further comprising a micro-pinhole array attached to the multi-spectral filter array for limiting an angle of light that is transmitted through the multi-spectral filter array.

13. The system of claim 3, wherein the multi-spectral filter array is divided into unit cells each comprising multi-spectral filters.

14. The system of claim 13, wherein each unit cell comprises at least nine filters of nine different spectral bands.

15. The system of claim 3, wherein the sensor array lies inside a detachable camera back of the optical system.

16. The system of claim 3, wherein the sensor array is a grey level sensor array.

17. The system of claim 3, wherein the sensor array is a color-coated sensor array.

18. The system of claim 3, wherein the long axis of the image of the eye tissue falls on at least 2592 pixels of the sensor array.

19. The system of claim 3, further including a computer capable of reconstructing the spectral images.

20. The system of claim 19, wherein reconstructing the spectral images includes de-mosaicking of spectral data from readings of the digital sensor array.

21. The system of claim 19, further including a program capable of analyzing the spectral images.

* * * * *